United States Patent [19]

Haire

[11] 4,256,742
[45] Mar. 17, 1981

[54] ANTIDEPRESSANT OXIME ETHERS OF DIBENZOCYCLOHEPTAZIRIDONES

[75] Inventor: Michael J. Haire, Newark, Del.

[73] Assignee: E. I. Du Pont de Nemours and Company, Wilmington, Del.

[21] Appl. No.: 51,341

[22] Filed: Jun. 27, 1979

Related U.S. Application Data

[63] Continuation-in-part of Ser. No. 937,716, Aug. 29, 1978, abandoned.

[51] Int. Cl.³ ............... C07D 203/26; A61K 31/445; A61K 31/395; C07D 203/02
[52] U.S. Cl. ............... 424/244; 260/239 E; 546/196; 544/111; 424/267; 424/274; 424/248.54; 424/248.56; 564/253; 568/373; 260/326.5 C
[58] Field of Search ............ 260/239 E, 326.5 C; 546/196; 544/111; 424/267, 244, 274, 248.54, 248.56

[56] References Cited

U.S. PATENT DOCUMENTS 4,123,546  10/1978  Haire ............... 260/239 E

Primary Examiner—Mark L. Berch

[57] ABSTRACT

Polycyclic aziridines, such as 0-[2-(dimethylamino)ethyl]oxime of 1a,10b-dihydrodibenzo-[3,4,6,7]cyclohept[1,2-b]-N-methylazirin-6(1H)-one, useful for alleviating depression in mammals.

24 Claims, No Drawings

ANTIDEPRESSANT OXIME ETHERS OF DIBENZOCYCLOHEPTAZIRIDONES

CROSS REFERENCE TO RELATED APPLICATIONS

This application is a continuation-in-part of my co-pending application Ser. No. 937,716, filed on Aug. 29, 1978, now abandoned.

BACKGROUND OF THE INVENTION

This invention relates to antidepressant polycyclic aziridines.

Mental illnesses include psychoses and neuroses. The symptoms requiring treatment include depression, anxiety, agitation and hallucinations. Drugs used particularly for treatment of both reactive and endogenous depressions include monoamine oxidase (MAO) inhibitors such as iproniazide, tranylcypramine, nialamide, phenelzine and pargyline and the non-MAO inhibiting tricyclic aromatic dibenzazepines such as imipramine and dibenzocycloheptadienes such as amitriptyline.

All of these drugs have side effects that limit their usefulness. The MAO inhibitors may cause tremors, insomnia, hyperhydrosis, agitation, hypermanic behavior, confusion, hallucinations, convulsions, orthostatic hypertension and death. They frequently cause dizziness, vertigo, headache, inhibition of ejaculation, difficulty in urination, weakness, fatigue, dry mouth, constipation and blurred vision. Imipramine may cause blurred vision, dryness of mouth, constipation, urinary retention, orthostatic hypotension, respiration depression, myocardial infarction and congestive heart failure. Similar difficulties are experienced with amitriptyline.

The present invention results from efforts to develop new psychotherapeutic agents which are effective and have fewer side effects than the drugs used today.

SUMMARY OF THE INVENTION

This invention relates to antidepressant compounds of formula I

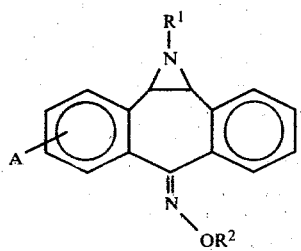

where
A is hydrogen, F, Cl, Br, $NO_2$, $CF_3$, $C_{1-4}$ alkyl or $C_{1-4}$ alkoxy;
$R^1$ is hydrogen, $C_{1-4}$ alkyl, $C_4$-$C_6$ cycloalkylmethyl, $C_{1-4}$ acyl or benzoyl; and
$R^2$ is

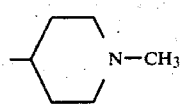

or $-(CH_2)_n NXY$;
where
n is 2 or 3; and
X and Y independently are hydrogen or $C_{1-4}$ alkyl, or together are linked to form $-(CH_2)_4-$, $-(CH_2)_5-$ or $-CH_2CH_2OCH_2CH_2-$; and
pharmaceutically suitable acid addition salts thereof.

Additionally this invention relates to compounds of the above scope of Formula I except $R^1$ and $R^2$ are hydrogen. These compounds are intermediates in preparation of the antidepressant compounds of formula I. The invention also includes a process for making the same.

DETAILED DESCRIPTION OF THE INVENTION

Preferred Compounds

Preferred antidepressant compounds are where, independently:
A is hydrogen; or
$R^1$ is hydrogen; or
$R^2$ is $-(CH_2)_n NXY$ wherein n is 2 and
X and Y independently are hydrogen or methyl.
More preferred antidepressant compounds are where
A is hydrogen and $R^1$ is hydrogen; or
A is hydrogen and $R^2$ is $-(CH_2)_n NXY$ where
n is 2 and
X and Y independently are hydrogen or methyl.
Most preferred antidepressant compounds are where
A is hydrogen,
$R^1$ is hydrogen, and
$R^2$ is $-(CH_2)_n NXY$ wherein
n is 2 and
X and Y independently are hydrogen or methyl.
A preferred intermediate compound is where $R^1$, $R^2$ and A are hydrogen.

PHARMACEUTICAL SALTS

Pharmaceutically suitable acid addition salts of the compounds of formula I include those made with physiologically acceptable acids that are known in the art; such salts include hydrochloride, sulfate, nitrate, phosphate, citrate, tartrate, maleate and the like.

SYNTHESIS

Preparation of compounds of formula I and intermediate compounds is described in conjunction with the following schematic. A, $R^1$ and $R^2$ are as previously defined.

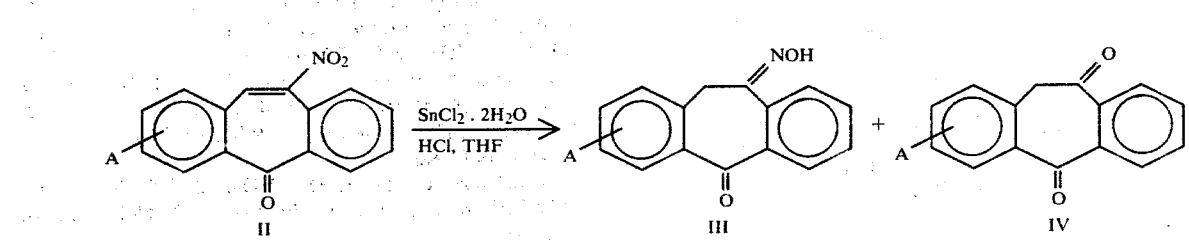

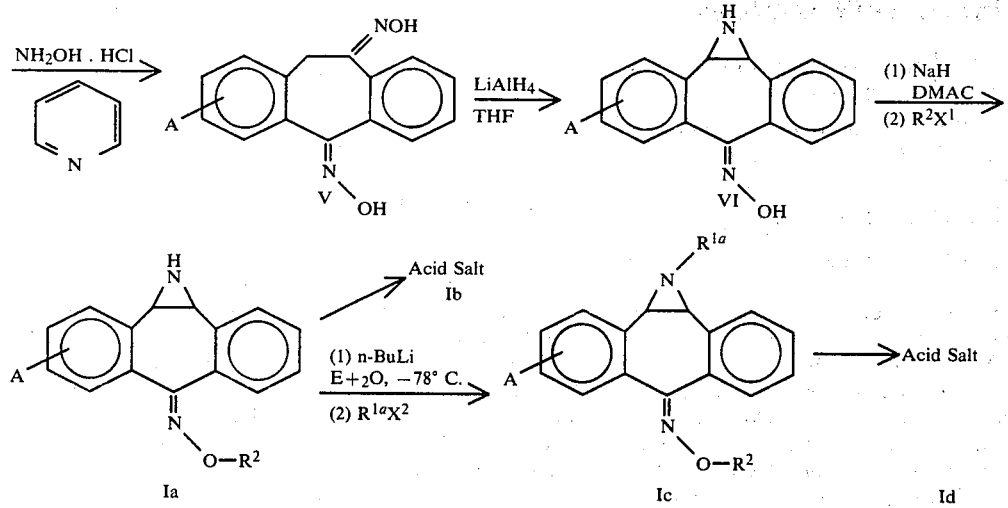

The preparation of the starting nitro-olefin II is described in U.S. Pat. No. 3,883,593. The nitro-olefin is treated with stannous chloride or stannous chloride dihydrate in a mixture of concentrated HCl and tetrahydrofuran (THF) at 0° to 25° C. for 1-24 hrs. resulting in a mixture of keto-oxime III and diketone IV. The mixture is refluxed with hydroxylamine hydrochloride in pyridine to give dioxime V which is refluxed with lithium aluminum hydride in tetrahydrofuran to give an aziridinyl oxime VI. The aziridinyl oxime is treated with base, preferably sodium hydride, in dry N,N-dimethylacetamide for 10-30 min., followed by an appropriate alkylating agent $R^2X^1(X^1=Cl,Br,I,$ tosylate), such as 2-dimethylaminoethyl chloride hydrochloride, which has been neutralized with an equivalent amount of sodium hydride in N,N-dimethylacetamide (DMAC), to give the antidepressant oxime ether Ia. Treatment of the oxime ether with hydrochloric acid in ethanol or tartaric acid in 2-propanol affords the acid salt Ib. The oxime ether Ia can be treated with base, preferably n-butyllithium, in diethyl ether at $-78°$, followed by addition of an appropriate alkylating agent $R^{1a}X^2(R^{1a}=R^1$ except for excluding $H;X^2=Cl,Br,I,$ tosylate) such as methyl iodide or acetyl chloride, to give the aziridine substituted oxime ether Ic. The acid salt Id of the aziridine substituted compounds is prepared as described above in preparation of Ib.

To further illustrate the present invention, the following examples are provided. All parts are by weight and temperatures are in degrees centigrade unless otherwise specified.

EXAMPLE 1

A.

10-Oximino-10,11-dihydro-5H-dibenzo[a,d]cyclohepten-5-one and
10,11-Dihydro-5H-dibenzo[a,d]cyclohepten-5,10-dione

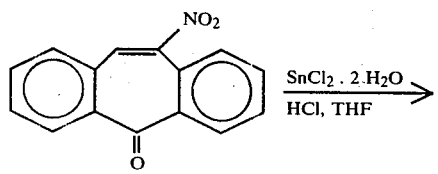

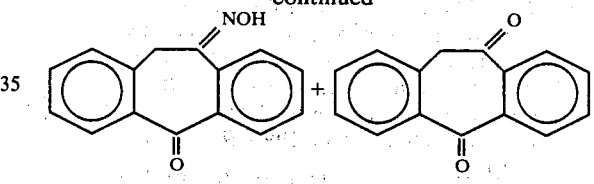

To a suspension of 150.00 g (0.60 mol) of 10-nitro-5H-dibenzo[a,d]cyclohepten-5-one in 1800 ml of THF at 0° was added slowly a pre-cooled solution of 406.08 g (1.80 mol) of stannous chloride dihydrate in 600 ml of THF and 600 ml of conc. HCl. The solution was stirred for 1.5 hr at 0° followed by 40 hr. at room temperature. The above procedure was repeated and the two reactions were combined, diluted with 6000 ml of $CH_2Cl_2$, washed with water (1×), 5% HCl, and water (2×). The organic layer was dried, treated with activated charcoal, filtered, and concentrated to give a black tar. The tar was taken up in 4500 ml of ether, treated with 150 g of anhydrous potassium carbonate, and enough water was added slowly to make a slurry with the potassium carbonate. The mixture was then slowly dried with additional potassium carbonate, filtered, and concentrated in vacuo to give an orange oil. The oil was crystallized from ethanol giving 159 g of a yellow solid which was a mixture of 10-oximino-10,11-dihydro-5H-dibenzo[a,d]cyclohepten-5-one and 10,11-dihydro-5H-dibenzo[a,d]cyclohepten-5,10-dione: NMR ($CDCl_3$/TMS) δ 8.50-7.10 (m, 8H, arom), 4.20 (s, 2H, benzylic H from dione), and 4.12 (s, 2H, benzylic H from oxime); IR ($CHCl_3$): 2.74, 2.97, 3.29, 5.92, 6.02, 6.29, 6.92, 7.82, 8.30, 8.68, 9.41, 9.82, 10.57, 10.89, 12.44, 14.14, and 14.42μ.

Anal. Calcd. for $C_{15}H_{11}NO_2$: 237.0789. Found: 237.0788. Calcd. for $C_{15}H_{10}O_2$: 222.0680. Found: 222.0687.

B.
5,10-Dioximino-10,11-dihydro-5H-dibenzo[a,d]cycloheptene

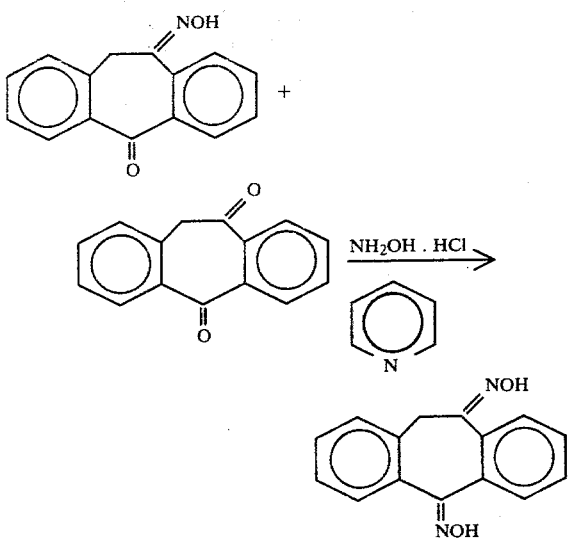

A mixture of 50.00 g of the product mixture from the stannous chloride reduction of 10-nitro-5H-dibenzo[a,d]cyclohepten-5-one and 62.61 g (0.901 mol) of hydroxylamine hydrochloride in 500 ml of pyridine was refluxed for 6 hr, poured into 3000 ml of ice water and 100 ml of conc. HCl, and extracted with CH$_2$Cl$_2$. The extracts were washed with brine, dried, treated with activated charcoal, filtered, and concentrated in vacuo to give a solid suspended in pyridine. The solid was removed by filtration and the pyridine treated as above to give a white solid. The solids were combined giving 44.09 g of 5,10-dioximino-10,11-dihydro-5H-dibenzo[a,d]cycloheptene as a white solid which had incorporated pyridine. The pyridine could not be removed by heating, high vacuum, or recrystallization: mp 220°–221°; NMR (DMSO-d$_6$/TMS) δ 11.62 (s, 1H, =NOH), 11.57 (s, 1H, =NOH), 7.50–7.00 (m, 8H, arom), and 3.97 (br s, 2H, benzylic); IR (CHCl$_3$) 2.79, 3.34, 6.33, 6.99, 8.20, 8.34, 9.39, 9.74, 10.09, 10.79, 12.65 and 14.34μ.

Anal. Calcd. for C$_{15}$H$_{12}$N$_2$O$_2$: 252.0898. Found: 252.0881.

C.
5-Oximino-10,11-dihydro-10,11-azacyclopropa-5H-dibenzo[a,d]cycloheptene

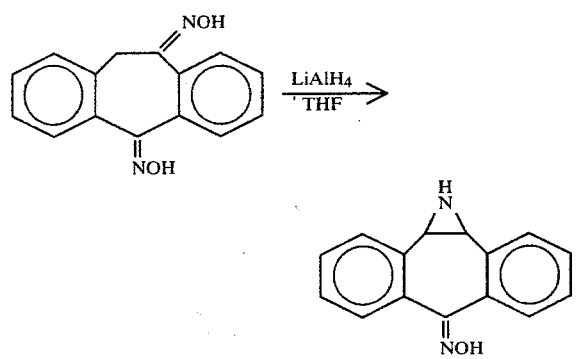

To a suspension of 67.86 g (1.79 mol) of lithium aluminum hydride in 1000 ml of dry tetrahydrofuran (THF) under N$_2$ was added carefully a solution of 75.00 g (0.298 mol) of 5,10-dioximino-10,11-dihydro-5H-dibenzo[a,d]cycloheptene in 3000 ml of dry THF. (The dioxime was contaminated with pyridine from its preparation but this does not interfere with the lithium aluminum hydride reduction). The mixture was stirred at room temperature for 4 hr, cooled with an ice bath, and 68 ml of ice water, 68 ml of cold 15% aqueous sodium hydroxide, and 204 ml of ice water were carefully added successively. After stirring for 30 min. more, the mixture was filtered, and solid which was present washed with THF and CH$_2$Cl$_2$. A second run was made as above, and the two filtrates and washings were combined and concentrated in vacuo to give a yellow solid. The solid was washed with ether (2×50 ml) and CHCl$_3$ (2×40 ml), filtered, and vacuum dried giving 23.84 g (0.101 mol, 17%) of 5-oximino-10,11-dihydro-10,11-azacyclopropa-5H-dibenzo-[a,d]cycloheptene as a white solid: mp 216°–217° (dec); NMR (DMSO-d$_6$/TMS) δ 10.83 (br s, 1H, =NOH), 7.60–7.00 (br m, 8H, arom), and 3.42 (br s, 3H, —NH— and benzylic); IR (CHCl$_3$) 2.77, 2.97, 3.34, 7.03, 8.21, 8.33, 9.61, 10.80, 12.66 and 14.08μ.

Anal. Calcd. for C$_{15}$H$_{12}$N$_2$O: 236.1002. Found: 236.0975. Calcd: C, 76.25; H, 5.12; N, 11.86. Found: C, 76.68; H, 5.08; N, 11.57.

EXAMPLE 2

O-[2-(Dimethylamino)ethyl]oxime of 1a,10b-dihydrodibenzo[3,4,6,7]cyclohept[1,2-b]azirin-6(1H)-one

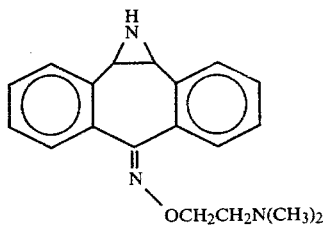

To a stirred suspension of 140 mg (5.82 mmol) of sodium hydride in 25 ml of N,N-dimethylacetamide (DMAC) which had been distilled from and stored over molecular sieves was added 1.36 g (5.76 mmol) of 5-oximino-10,11-dihydro-10,11-azacyclopropa-5H-dibenzo[a,d]cycloheptene under N$_2$. After stirring for 15 min. a mixture of 140 mg of sodium hydride and 835 mg (5.80 mmol) of N,N-dimethylaminoethyl chloride hydrochloride in 25 ml of DMAC was added. The mixture was stirred for 26 hr, poured into 200 ml of brine, and extracted with methylene chloride. The organic extracts were washed with brine, dried, treated with activated charcoal, filtered, and concentrated in vacuo to give a light yellow oil which crystallized overnight. The solid was washed with ether, filtered, and vacuum dried giving 1.12 g (3.65 mmol, 63%) of O-[2-(dimethylamino)ethyl]oxime of 1a,10b-dihydrodibenzo[3,4,6,7]cyclohept[1,2-b]azirin-6(1H)-one as a white solid, mp 110°–117°.

EXAMPLE 3

O-[2-(Dimethylamino)ethyl]oxime of 1a,10b-Dihydrodibenzo-[3,4,6,7]cyclohept[1,2-b]-N-methylazirin-6(1H)-one

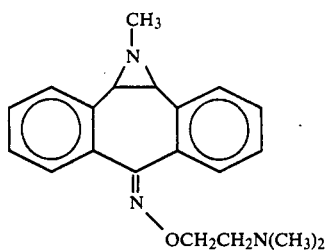

To a suspension of 0.50 g (1.63 mmol) of O-[2-(dimethylamino)ethyl]oxime of 1a,10b-dihydrodibenzo[3,4,6,7]cyclohept[1,2-b]azirin-6(1H)-one in 60 ml of ether under N$_2$ at −78° was added 1.76 mmol of n-butyl-lithium in hexane. After stirring for 5 min, 0.11 ml (1.77 mmol) of methyl iodide was added. The mixture was allowed to return to room temperature with stirring for 2 hr. The ether was removed in vacuo to give a white solid. The solid was taken up in methylene chloride, washed with brine, dried, filtered, and concentrated in vacuo to give 0.43 g (1.34 mmol, 82%) of the title compound as a clear thick oil: NMR (CDCl$_3$/TMS) δ 7.60–7.10 (m, 8H, arom), 4.33 (t, 2H, J=6 Hz, —OCH$_2$—), 2.70 (t, 2H, J=6 Hz, —CH$_2$N(CH$_3$)$_2$), 2.70 (s, 2H, benzylic), 2.51 (s, 3H, —NCH$_3$), and 2.28 (s, 6H, —N(CH$_3$)$_2$); IR (CHCl$_3$) 3.30, 6.82, 7.50, 8.20, 8.50, 9.31, 9.62, 10.20, 10.72, 12.61, and 14.00μ.

EXAMPLE 4

O-[2-(Dimethylamino)ethyl]oxime of 1a,10b-dihydrodibenzo[3,4,6,7]cyclohept[1,2-b]-N-benzoylazirin-6(1H)-one

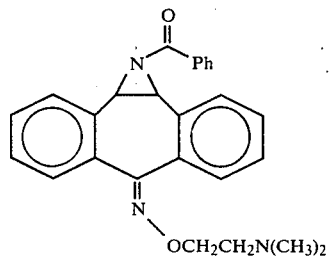

Similar procedure and amounts as in the synthesis of Example 3 were used except 0.20 ml (1.72 mmol, 0.24 g) of benzoyl chloride was used instead of methyl iodide. The product was 0.69 g (1.68 mmol, 100%) of the title compound as a milky yellow oil: NMR (CDCl$_3$/TMS) 8.20–7.10 (m, 13H, arom), 4.63 (br t, 2H, J=4 Hz, —OCH$_2$—), 4.10 (d, 1H, J=6.5 Hz, benzylic), 3.96 (d, 1H, J=6.5 Hz, benzylic), 3.20 (br t, 2H, J=4 Hz, —CH$_2$N(CH$_3$)$_2$), and 2.50 (s, 6H, —N(CH$_3$)$_2$); IR (CHCl$_3$) 3.42, 6.01, 6.31, 6.99, 7.20, 7.69, 7.87, 8.01, 8.26, 9.31, 9.43, 10.33, 10.86, 11.00, 12.71, and 14.29μ.

Anal. Calc for C$_{26}$H$_{25}$N$_3$O$_2$: 411.1945. Found: 411.1940.

EXAMPLE 5

O-[2-(Dimethylamino)ethyl]oxime of 1a,10b-dihydrodibenzo[3,4,6,7]cyclohept[1,2-b]-N-acetylazirin-6(1H)-one

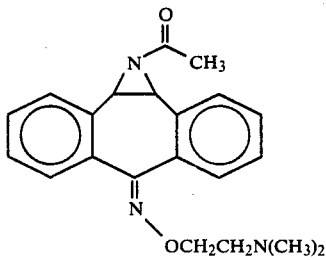

Similar procedure and amounts as in the synthesis of Example 3 were used except 0.13 ml (0.14 g, 1.83 mmol) of acetyl chloride was used instead of methyl iodide. The product was 0.40 g (1.15 mmol, 70%) of the title compound as a light yellow oil: NMR (CDCl$_3$/TMS) δ 7.60–7.10 (m, 8H, arom), 4.59 (t, 2H, J=4.5 Hz, —OCH$_2$—), 3.92 (s, 2H, benzylic), 3.18 (t, 2H, J=4.5 Hz, —CH$_2$N(CH$_3$)$_2$), 2.58 (s, 6H, —N(CH$_3$)$_2$), and 2.15 (s, 3H, —COCH$_3$); IR (CHCl$_3$) 3.43, 5.97, 6.20, 6.91, 7.16, 7.41, 8.01, 8.29, 8.75, 9.66, 10.35, 11.07, 12.76, and 14.11μ.

Anal. Calc for C$_{21}$H$_{23}$N$_3$O$_2$: 349.1789. Found: 349.1769.

EXAMPLES 6 TO 15

Following the procedure of Example 2 except for replacement of N,N-dimethylaminoethyl chloride with the named alkylating agent below, the following compounds of Formula I were prepared.

| Example No. | Alkylating Agent | Oxime Ether |
|---|---|---|
| 6 | ClCH$_2$CH$_2$N(CH$_3$)$_2$ · HCl | ![structure] |
| | Yield | Product Characteristics |
| | 63% | m.p. 110–117°<br>NMR (CDCl$_3$/TMS) δ 7.50–7.00 (m, 8H, arom), 4.25 (t, 2H, J = 6Hz, —OCH$_2$—), 3.40 (br s, |

-continued

| Example No. | | |
|---|---|---|
| | | 2H, benzylic), 2.64 (t, 2H, J = 6Hz, —CH₂—N—), 2.60–2.35 (br hump, 1H, —NH—), and 2.23 (s, 6H, —N(CH₃)₂). IR (nujol) 3.08, 3.40, 7.82, 8. 8.30, 8.55, 9.24, 9.61, 10.22 10.93, 12.85, and 13.40μ. Anal. Calcd. for C₁₉H₂₁N₃O: 307.1683. Found: 307.1670. Calcd: C, 74.24; H, 6.89; N, 13.67. Found: C, 73.81; H, 6.89; N, 13.39. |
| 7 | Alkylating Agent ClCH₂CH₂NH₂ . HCl | Oxime Ether  (tricyclic structure with NH bridge, =N—OCH₂CH₂NH₂) |
| | Yield 66% | Product Characteristics m.p. 115° (foaming) NMR (CDCl₃/TMS) δ 7.50–7.00 (m, 8H, arom), 4.14 (t, 2H, J = 5 Hz, —OCH₂—), 3.38 (s, 2H, benzylic), 2.88 (t, 2H, J = 5Hz, —CH₂—NH₂), and 1.80–1.45 (br hump, 3H, —NH— and —NH₂). IR (CHCl₃) 3.30 (br), 6.09, 6.69, 8.15, 8.30, 9.30, 10.25, 10.75, 12.64, and 14.01μ. Anal. MS No molecular ion detected |
| 8 | Alkylating Agent ClCH₂CH₂NHCH₃ . HCl | Oxime Ether (tricyclic structure with NH bridge, =N—OCH₂CH₂NHCH₃) |
| | Yield 46% | Product Characteristics m.p. 146–150° NMR (CDCl₃/TMS) δ 7.50–7.00 (m, 8H, arom), 4.24 (t, 2H, J = 5Hz, —OCH₂—), 3.40 (s, 2H, benzylic), 3.50–3.10 (br hump, 2H, —NH—), 2.81 (t, 2H, J = 5Hz, —CH₂—NH—), and 2.31 (s, 3H, —NHCH₃). IR (CHCl₃) 2.99, 3.30, 6.10, 6.70 8.20, 8.30, 9.55, 10.29, 10.80, 12.67, and 14.00μ. Anal. Calcd. for C₁₈H₁₉N₃O: 293.1527. Found: 293.1553. |
| 9 | Alkylating Agent ClCH₂CH₂CH₂N(CH₃)₂ . HCl | Oxime Ether (tricyclic structure with NH bridge, =N—OCH₂CH₂CH₂N(CH₃)₂) |
| | Yield 70% | Product Characteristics m.p. 157–160° NMR (DMSO-d₆/TMS) δ 7.60–7.00 (m, 8H, arom), 4.10 (t, 2H, J = 6Hz, —OCH₂—), 3.40 (br s, 3H, benzylic and —NH—), 2.48 (t, 2H, J = 6Hz, —CH₂—N(CH₃)₂), 2.10 (s, 6H, —N(CH₃)₂), and 2.20–1.50 (m, 2H, —CH₂CH₂CH₂—). |

| Example No. | | |
|---|---|---|
| | | IR (nujol) 3.10, 3.44, 6.80, 7.45 7.90, 8.26, 8.50, 8.60, 9.24, 9.36, 9.95, 10.18, 10.30 and 13.39μ. Anal. MS molecular ion at m/e 321 |
| 10 | Alkylating Agent<br>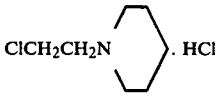 | Oxime Ether<br>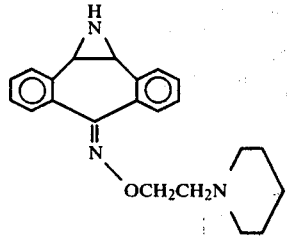 |
| | Yield<br>18% | Product Characteristics<br>m.p. 150–160°<br>NMR (CDCl$_3$/TMS) δ 7.60–7.00 (m, 8H, arom), 4.33 (t, 2H, J = 6Hz, —OC$\underline{H}_2$—), 3.30 (br s, 3$\underline{H}$, benzylic and —N$\underline{H}$—), 2.68 (t, 2$\underline{H}$, $\underline{J}$ = 6Hz,<br><br>—C$\underline{H}_2$—N—), 2.60–2.30 (m, 4$\underline{H}$,<br><br>—CH$_2$—N—CH$_2$), and 1.80–1.17 (m, 6$\underline{H}$, —C$\underline{H}_2$CH$_2$C$\underline{H}_2$—).<br>IR (CHCl$_3$) 3.03, 3.44, 6.73, 6.90, 7.56, 8.17, 8.57, 9.60, 10.25, 10.90, 12.66, and 14.05μ.<br>Anal. MS molecular ion at m/e 347. |
| 11 | Alkylating Agent<br>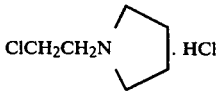 | Oxime Ether<br>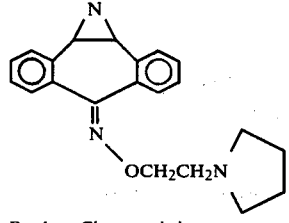 |
| | Yield<br>9% | Product Characteristics<br>NMR (CDCl$_3$/TMS) δ 7.50–7.00 (m, 8H, arom), 4.31 (t, 2$\underline{H}$, $\underline{J}$ = 6Hz, —O—C$\underline{H}_2$—), 3.85–3.10 (br hump, 1$\underline{H}$, —N$\underline{H}$—), 3.40 (s, 2$\underline{H}$, benzylic),<br><br>2.87 (t, 2$\underline{H}$, $\underline{J}$ = 6Hz, —C$\underline{H}_2$—N—), 2.80–2.45 (m, 4H, —CH$_2$—N—CH$_2$—), and 1.90–1.55 (m, 4$\underline{H}$, —C$\underline{H}_2$C$\underline{H}_2$—).<br>IR (CHCl$_3$) 3.07, 3.41, 6.13, 6.76, 6.88, 7.58, 8.18, 8.58, 9.48, 9.67, 10.28, 11.04, 12.68 and 14.43μ.<br>Anal. MS molecular ion at m/e 333. |
| 12 | Alkylating Agent<br>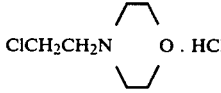 | Oxime Ether<br>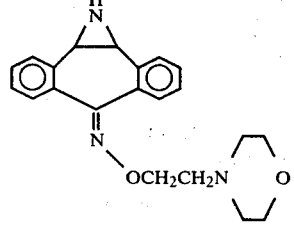 |
| | Yield<br>63% | Product Characteristics<br>m.p. 141–145°<br>NMR (DMSO-d$_6$/TMS) δ 7.60–7.05 (m, 8$\underline{H}$, arom), 4.15 (t, 2$\underline{H}$, $\underline{J}$ = 6Hz, —O—C$\underline{H}_2$—), 3.70–3.25 (m, 7$\underline{H}$, —C$\underline{H}_2$—O—C$\underline{H}_2$—, —NH—, and |

| Example No. | | |
|---|---|---|
| | | benzylic), 2.58 (t, 2H, J = 6Hz, —CH₂N—), and 2.65–2.20 (m, 4H, —CH₂—N—CH₂—). IR (nujol) 3.10, 3.45, 7.70, 7.89, 8.30, 8.74, 9.00, 9.54, 9.61, 10.23, 10.60, 10.90, 11.70, 12.61, 12.90, and 13.42μ. Anal. MS molecular ion at m/e 349. |
| 13 | Alkylating Agent 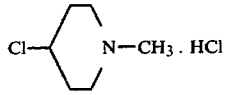 | Oxime Ether 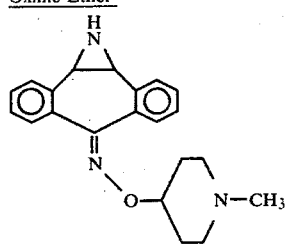 |
| | Yield 6% | Product Characteristics NMR (CDCl₃/TMS) δ 7.60–7.00 (m, 8H, arom), 4.55–4.10 (m, 1H, —O—CH—), 3.70–3.35 (m, 3H, —NH— and benzylic), and 3.30 = 1.70 (m, 11H, —CH₂CH₂N(CH₃)CH₂CH₂—). IR (CHCl₃) 3.02, 3.42, 6.86, 7.37, 7.57, 7.89, 8.19, 8.57, 9.47, 9.63, 10.32, 11.03, 12.67 and 14.12μ. Anal. MS molecular ion at m/e 333. |
| 14 | Alkylating Agent ClCH₂CH₂NHEt . HCl | Oxime Ether 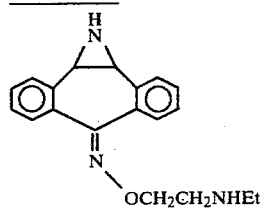 |
| | Yield 54% | Product Characteristics mp 125–139° NMR (CDCl₃/TMS) δ 7.60–7.00 (m, 8H, arom), 4.28 (t, 2H, J = 5.5 Hz, —OCH₂—), 3.34 (br s, 2H, benzylic), 3.05–2.65 (br hump, 4H, —CH₂NHEt and aziridinyl NH), 2.61 (q, 2H, J = 7 Hz, —CH₂CH₃), and 1.00 (t, 3H, J = 7 Hz, —CH₂CH₃). IR (nujol) 3.12, 3.44, 6.92, 7.35, 8.37, 8.62, 9.35, 9.67, 10.27, 10.70, 10.97, 12.70, and 13.47μ. Anal. MS molecular ion at m/e 349. |
| 15 | Alkylating Agent ClCH₂CH₂NHBu . HCl | Oxime Ether 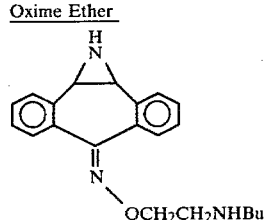 |
| | Yield 91% | Product Characteristics mp 112–114° C. NMR (CDCl₃/TMS) δ 7.50–7.10 (m, 8H, arom), 4.30 (t, 2H, J = 5.5Hz, —OCH₂—), 3.48 (br s, 2H, benzylic), 2.91 (t, 3H J = 5.5Hz, —CH₂—NH— and aziridinyl NH), 2.62 (br t, 3H, J = 7Hz, —NHCH₂—C₃H₇), 1.70–1.05 (m, 4H, —CH₂CH₂—CH₂CH₃), and 0.85 (br | t, 3H, J = 6Hz, —CH₃).
IR(CHCl₃) 2.92, 3.36, 6.09, 6.69,
6.87, 8.16, 8.33, 8.54, 9.59, 10.22,
12.57, and 14.29 μ.

EXAMPLE 16

Tartaric acid Salt of O-[2-(dimethylamino)ethyl]oxime of 1a,10b-dihydrodibenzo[3,4,6,7]cyclohept[1,2-b]-N-methylazirin-6(1H)-one.

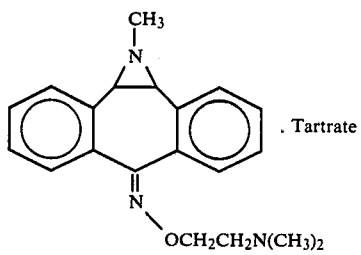
. Tartrate

To a hot solution of 0.15 g. (1.0 mmol) of tartaric acid in 10 ml of 2-propanol was added a hot solution of 0.31 g (0.96 mmol) of O-[2-(dimethylamino)-ethyl]oxime of 1a,10b-dihydrodibenzo[3,4,6,7]cyclohept-[1,2-b]-N-methylazirin-6(1H)-one in 10 ml of 2-propanol. The solution was allowed to return to room temperature over one hour. The volume was reduced to 10 ml under a stream of N₂, and solid which was present was filtered and vacuum dried giving 0.22 g (0.47 mmol, 49% of the title compound as an off-white, watersoluble solid, mp 75°–80° (foaming); NMR (DMSO-d₆/TMS) δ7.60–7.10 (m, 8H arom), 5.70–5.25 (br s, 4H, —OH), 4.35 (t, 2H, J=5.5 Hz, —O—CH₂—), 4.13 (s, 2H, —CHOH—), 3.30–2.95 (br m, 2H, —CH₂—N(CH₃)₂), 3.00 (s, 2H, benzylic), 2.57 (s, 3H, —NCH₃—), and 2.51 (s, 6H, —N(CH₃)₂); approximately 1 equivalent of 2-propanol was present in the solid.

EXAMPLES 17 to 20

The procedure of Example 16 was followed in preparation of tartrate salts with substitution of the appropriate compound of Formula I.

For preparation of the hydrochloride salt in the table below, 0.50 g of the appropriate compound of Formula I was stirred in 125 ml of 3 N HCl in ethanol for three hours. The solvent was removed in vacuo leaving a gum. Acetone treatment (25 ml) gave the resulting salt as a solid.

| Example No. | | |
|---|---|---|
| | Salt | Yield |
| 17 | 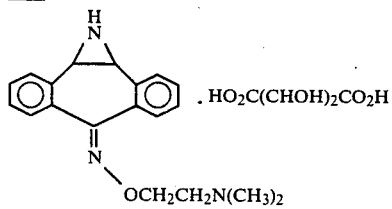 . HO₂C(CHOH)₂CO₂H | 100% |

Product Characteristics
m.p. 161–163° (sintering), 195° C. (foaming)
NMR (DMSO-d₆/TMS) δ 7.60–7.10 (m, 8H, arom),
7.00–6.35 (br hump, 5H, —NH—, —CO₂H, —OH),
4.32 (t, 2H, J = 5Hz, —O—CH₂—), 4.10 (s, 2H,
—CHOH—), 3.48 (s, 2H, benzylic), 3.08 (t, 2H,
J = 5Hz, —CH₂—N(CH₃)₂), and 2.54 (s, 6H, —N(CH₃)₂)
Water Soluble
Incorporates 2-propanol

| | Salt | Yield |
|---|---|---|
| 18 | 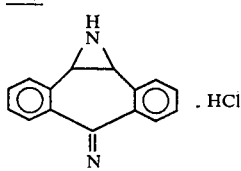 . HCl | 79% |

Product Characteristics
m.p. 130° (foaming)
Water Soluble

| | Salt | Yield |

-continued

| Example No. | | |
|---|---|---|
| 19 | 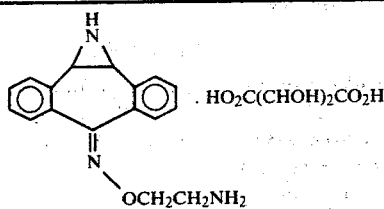 . HO$_2$C(CHOH)$_2$CO$_2$H | 74% |

Product Characteristics
m.p. 95° (foaming)
NMR (DMSO-d$_6$/TMS) δ 7.60–7.00 (m, 8H, arom),
6.90–5.80 (br hump, 7H, —NH—, —NH$_2$, —CO$_2$H, —OH),
4.40–4.00 (br m, 2H, —OCH$_2$—), 4.00 (br s, 2H,
—CHOH—), 3.50 (br s, 2H, benzylic), and 3.35–2.95
(br m, 2H, —CH$_2$NH$_2$).
Water Soluble
Incorporates 2-propanol
Salt                                                                                     Yield

| 20 | 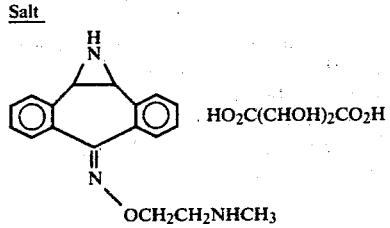 . HO$_2$C(CHOH)$_2$CO$_2$H | 38% |

Product Characteristics
m.p. Foaming to 270°
NMR (DMSO-d$_6$/TMS) δ 7.70–7.00 (m, 8H, arom),
7.20–6.40 (br hump, 6H, —NH—, —NHCH$_3$,
—CO$_2$H, —OH), 4.33 (br t, 2H, J = 5Hz, —OCH$_2$—),
4.11 (s, 2H, —CHOH—), 3.52 (s, 2H, benzylic),
3.23 (br t, 2H, J = 5Hz, —CH$_2$—NHCH$_3$), and 2.58
(s, 3H, —NHCH$_3$).
IR (nujol) 3.05, 3.40, 5.77, 6.20, 7.27, 8.89,
9.30, 10.25, 10.55, and 13.37μ.
Water Soluble
Incorporates 2-propanol

EXAMPLE 21

O-[2-(Dimethylaminoethyl]oxime of 1a,10b-dihydrodibenzo[3,4,6,7]cyclohept[1,2-b]-N-(cyclopropylmethylazirin-6(1H)-one

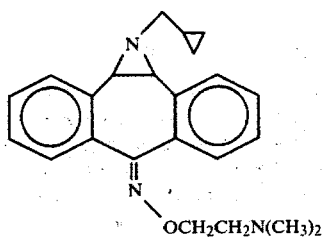

Similar procedure and amounts as in Example 3 were used except 0.32 g (1.76 mmol) of iodomethylcyclopropane was used instead of methyl iodide. The product was 0.49 g of yellow foam which was chromatographed on a 20 cm×20 cm×2 mm plate of silica gel. After chloroform development, the fastest moving band was collected giving 0.10 g (0.28 mmol, 17%) of the title compound as a yellow oil: NMR (CDCl$_3$/TMS) δ7.60–7.10 (m, 8H, arom), 4.35 (t, 2H, J=6 Hz, —OCH$_2$—), 2.77 (t, 2H, J=6 Hz, $$-CH_2CH_2\overset{|}{N}-),$$

2.79 (s, 2H, benzylic), 2.85–2.45 (m, 2H, $$-CHCH_2\overset{|}{N}-),$$

2.32 (s, 6H, —N(CH$_3$)$_2$), and 1.60–0.68 (m, 5H, cyclopropyl).

EXAMPLE 22

O-[2-Dimethylamino)ethyl]oxime of 1a,10b-dihydrodibenzo[3,4,6,7]cyclohept[1,2-b]-N-(cyclobutylmethyl)azirin-6(1H)-one

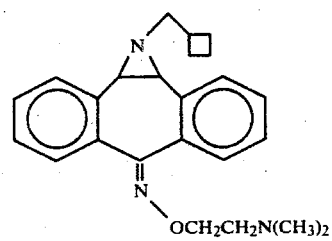

Similar procedure and amount as in Example 3 were used except 0.42 g (1.75 mmol) of methylcyclobutyl tosylate was used instead of methyl iodide. The product, 0.67 g of yellow oil, was chromatographed as in Example 21. The second slowest band was collected giving 0.10 g (0.27 mmol, 16%) of the title compound as a yellow oil: NMR (CDCl$_3$/TMS) $\delta$7.60–7.05 (m, 8H, arom), 4.30 (t, 2H, J=6 Hz, —OCH$_2$—), 2.85–2.38 (m, 6H,

and benzylic), 2.50 (s, 6H, —N(CH$_3$)$_2$), and 2.00–1.65 (m, 7H, cyclobutyl).

Dosage Forms

Dosage forms (compositions) suitable for internal administration contain from about 10 milligrams to about 50 milligrams of active ingredient per unit. In these pharmaceutical compositions, the active ingredient comprising one or more active compounds of this invention will ordinarily be present in an amount of about 0.1–90% by weight based on the total weight of the composition.

The active ingredient can be administered orally in solid dosage forms, such as capsules, tablets and powders, or in liquid dosage forms, such as elixirs, syrups and suspensions; it can also be administered parenterally, in sterile liquid dosage forms; or rectally in the form of suppositories.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, or ascorbic acid either alone or combined are suitable stabilizing agents. Also used are citric acid and its salts and sodium EDTA (ethylenediaminetetraacetic acid). In addition, parenteral solutions can contain preservatives, such as benzalkonium chloride, methyl- or propyl-paraben, and chlorobutanol.

Suppositories contain the active ingredient in a suitable oleaginous or water-soluble base. The oleaginous class includes cocoa butter and fats with similar properties; the water-soluble class includes polyethylene glycols.

Suitable pharmaceutical carriers are described in Remington's Pharmaceutical Sciences, E. W. Martin, a standard reference text in this field.

Useful pharmaceutical dosage-forms for administration of the compounds of this invention can be illustrated as follows:

CAPSULES

Capsules can be prepared by filling standard two-piece hard gelatin capsules with the following mixture using conventional encapsulating equipment:
Active ingredient, 25 mg.
Lactose, 200 mg.
Talc, 24 mg.
Magnesium Stearate, 6 mg.

A mixture of active drug in soy bean oil is prepared and injected by means of a positive displacement pump in gelatin to form soft gelatin capsules containing 25 mg. of the active ingredient. The capsules are washed in petroleum ether and dried.

TABLETS

Tablets can be prepared by conventional procedures so that each unit will contain:
Active ingredient, 25 mg.
Spray dried lactose, 300 mg.
Microcrystalline cellulose, 70 mg.
Magnesium stearate, 6 mg.

PARENTERALS

Parenteral composition suitable for intra muscular administration can be prepared so that each 2 mls. contains:
Active ingredient, 25 mg.
Sodium carboxyl methyl cellulose, 0.75%
Polysorbate 80, 0.04%
Benzyl alcohol, 0.9%
Sodium chloride, 1.8%
Water for Injection QS, 2 ml.

SUSPENSION

An aqueous suspension can be prepared using the base for oral administration so that each 5 mls. contain:
Active ingredient, 25 mg.
Methyl cellulose, 5%
Carboxy methyl cellulose, 5%
Syrup, 30%
Polysorbate 80, 0.2%
Cherry Flavor, 0.1%
Sodium benzoate, 5 mg.
Water QS, 5 mls.

USE

The compounds of the invention of formula I have antidepressant activity in the mammalian central nervous system as shown by their antidepressant activity in mice. They can be employed in compositions comprising one or more compounds of this invention as the active medicament and one or more non-toxic pharmaceutical carriers.

The compounds can be administered as treatment for psychiatric depressions of the reactive and endogenous types by any means that effects contact of the active ingredient compound with the site of action in the body of a warm-blooded animal. The compounds of this invention can be administered orally at doses of about 0.01–100.0 mg/kg or preferably at about 0.05–25.0 mg/kg or more preferably at about 0.2–10 mg/kg. The compounds can also be given parenterally. The useful human daily dose is expected to be in the range of 25–300 mg/kg. The dosage administered will be dependent upon the age, health, and weight of the recipient, the type and severity of depression, kind of concurrent treatment, if any, frequency of treatment and nature of the effect desired.

The antidepressant activity of the compounds is evidenced by tests conducted in female white mice in which prevention of tetrabenazine-induced sedation and depression is demonstrated. This mouse test is predictive of human antidepressant response (Everett, "The Dopa Response Petentiation Test and Its Use in Screening for Antidepressant Drugs", pp. 164–167 in "Antidepressant Drugs" [Proceedings of the First International Symposium], S. Garattini and M. N. G. Dukes, eds. 1967).

EXAMPLE A

Groups of 10 Carworth $CF_1S$ female mice, 18–21 g each, were fasted 1.5 hours and were intubated with antagonist compounds at oral doses of 0, 0.33, 1, 3, 9, 27, and 81 mg/kg in 0.20 ml of 1% Methocel. The mice were challenged 30 minutes later with tetrabenazine (as the methane-sulfonate), 32 mg/kg intraperitoneally (dissolved in 0.20 ml 0.05 M KCl at pH 2.0). One hour after antagonist (30 minutes after tetrabenazine), the mice were examined for signs of exploratory activity and ptosis (eyelid closure). Normal exploratory activity (relief from sedation) was recorded when a mouse lifted by the tail from a group of 10 in a testing box and placed on a stainless steel testing box lid (12.5"×8" with 0.33" mesh) either turned its head horizontally 30° in both directions or moved to the edge of the screen within 10 seconds after being placed on the screen. Relief from ptosis was recorded when exactly two seconds after placing the mouse facing the observer, lid closure was less than 50% in both eyes. Table 1 gives the results in mg/kg for examples of the invention and for the established standard antidepressant, amitriptyline.

TABLE 1

ED50 IN ANTITETRABENAZINE TEST

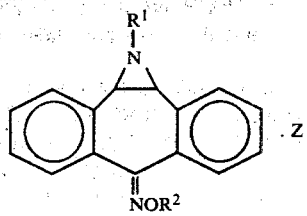

| $R^2$ | $R^1$ | Z | BLOCKADE OF Ptosis | Explor. |
|---|---|---|---|---|
| $CH_2CH_2NH_2$ | H | — | 1.3 | 6.6 |
| $CH_2CH_2NH_2$ | H | (Tartrate i-PrOH) | 3.4 | 14. |
| $CH_2CH_2NHCH_3$ | H | — | 0.57 | 1.9 |
| $CH_2CH_2NHCH_3$ | H | (Tartrate i-PrOH) | 1.3 | 6.2 |
| $CH_2CH_2NHC_2H_5$ | H | — | 4.3 | 9.0 |
| $CH_2CH_2N(CH_3)_2$ | H | — | 0.65 | 1.1 |
| $CH_2CH_2N(CH_3)_2$ | H | . HCl | 1.0 | 2.2 |
| $CH_2CH_2N(CH_3)_2$ | H | . Tartrate | 0.33 | 0.57 |
| $CH_2CH_2N(CH_3)_2$ | $CH_3$ | — | 0.65 | 0.93 |
| $CH_2CH_2N(CH_3)_2$ | $CH_3$ | . Tartrate | 0.93 | 2.7 |
| $CH_2CH_2N(CH_3)_2$ | $\overset{O}{\underset{\|}{C}}-CH_3$ | — | 13. | 19. |

TABLE 1-continued

ED50 IN ANTITETRABENAZINE TEST

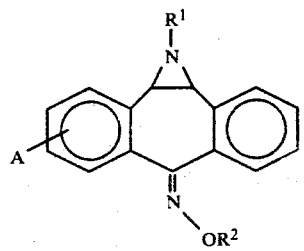

| $R^2$ | $R^1$ | Z | BLOCKADE OF Ptosis | Explor. |
|---|---|---|---|---|
| $CH_2CH_2N(CH_3)_2$ | $\overset{O}{\underset{\|}{C}}-\phi$ | — | 5.2 | 5.5 |
| $CH_2CH_2N\diagdown\!\!\diagup\!\!6$ | H | — | 8.3 | >81. |
| $CH_2CH_2N\diagdown\!\!\diagup\!\!O$ | H | — | 5.2 | 16. |
| $CH_2CH_2CH_2N(CH_3)_2$ | H | . | 18. | 32. |
| $CH_2CH_2N(CH_3)_2$ | — | $CH_2\triangle$ | 10.8 | 11.8 |
| $CH_2CH_2N(CH_3)_2$ | — | $CH_2\diamondsuit$ | 10.8 | 16 |
| $CH_2CH_2NHC_4H_9$ | H | — | 13.3 | >81 |
| AMTRIPTYLINE | | | 1.2 | 2.6 |

"Consisting essentially of" is intended to have its customary meaning: namely, that all specified materials and conditions are very important in practicing the invention but that unspecified materials and conditions are not excluded so long as they do not prevent the benefits of the invention from being realized.

What is claimed is:

1. A compound of the formula

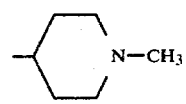

where
A is H, F, Cl, Br, $NO_2$, $CF_3$, $C_{1-4}$alkyl or $C_{1-4}$alkoxy;
$R^1$ is H, $C_{1-4}$alkyl, $C_4$-$C_6$ cycloalkylmethyl, $C_{1-4}$acyl or benzoyl;
$R^2$ is $$-\!\!\diagup\diagdown\!\!\mathrm{N-CH_3}$$

or $-(CH_2)_nNXY$
wherein
n is 2 or 3,

X and Y independently are H or $C_{1-4}$alkyl or together are linked to form —$(CH_2)_4$—, —$(CH_2)_5$— or —$CH_2CH_2OCH_2CH_2$—; or a pharmaceutically suitable acid addition salt thereof.

2. The compound of claim 1 which is the tartaric salt of O-[2-(dimethylamino)ethyl]oxime of 1a,10b-dihydrodibenzo[3,4,6,7]cyclohept[1,2-b]azirin-6(1H)-one.

3. A compound of claim 1 where A is hydrogen.

4. A compound of claim 1 where $R^1$ is hydrogen.

5. A compound of claim 1 where $R^2$ is —$(CH_2)_n$NXY wherein n is 2 and X and Y independently are hydrogen or methyl.

6. A compound of claim 1 where A is hydrogen and $R^1$ is hydrogen.

7. A compound of claim 1 where A is hydrogen, and $R^2$ is —$(CH_2)_n$NXY where n is 2 and X and Y independently are hydrogen or methyl.

8. A compound of claim 1 where

A is hydrogen;

$R^1$ is hydrogen; and $R^2$ is —$(CH_2)_n$NXY wherein n is 2; and

X and Y independently are hydrogen or methyl.

9. A pharmaceutical composition consisting essentially of a pharmaceutically suitable diluent and an antidepressant amount of a compound of claim 7.

10. A pharmaceutical composition consisting essentially of a pharmaceutically suitable diluent and an antidepressant amount of a compound of claim 8.

11. A pharmaceutical composition consisting essentially of a pharmaceutically suitable diluent and an antidepressant amount of a compound of claim 1.

12. A pharmaceutical composition consisting essentially of a pharmaceutically suitable diluent and an antidepressant amount of a compound of claim 3.

13. A pharmaceutical composition consisting essentially of a pharmaceutically suitable diluent and an antidepressant amount of a compound of claim 4.

14. A pharmaceutical composition consisting essentially of a pharmaceutically suitable diluent and an antidepressant amount of a compound of claim 5.

15. A pharmaceutical composition consisting essentially of a pharmaceutically suitable diluent and an antidepressant amount of a compound of claim 6.

16. A pharmaceutical composition consisting essentially of a pharmaceutically suitable diluent and an antidepressant amount of the compound of claim 2.

17. A method for treating depression in a mammal which comprises administering to the mammal an antidepressant amount of the compound of claim 16.

18. A method for treating depression in a mammal which comprises administering to the mammal an antidepressant amount of a compound of claim 11.

19. A method for treating depression in a mammal which comprises administering to the mammal an antidepressant amount of a compound of claim 12.

20. A method for treating depression in a mammal which comprises administering to the mammal an antidepressant amount of a compound of claim 13.

21. A method for treating depression in a mammal which comprises administering to the mammal an antidepressant amount of a compound of claim 14.

22. A method for treating depression in a mammal which comprises administering to the mammal an antidepressant amount of a compound of claim 15.

23. A method for treating depression in a mammal which comprises administering to the mammal an antidepressant amount of a compound of claim 9.

24. A method for treating depression in a mammal which comprises administering to the mammal an antidepressant amount of a compound of claim 10.

* * * * *